United States Patent [19]

Bloom et al.

[11] Patent Number: 5,639,653
[45] Date of Patent: Jun. 17, 1997

[54] METHOD FOR PROLIFERATING Vγ2Vδ2 T CELLS

[75] Inventors: Barry R. Bloom, Hastings-on-Hudson; Yoshimasa Tanaka, Bronx, both of N.Y.; Shigetoshi Sano, Nishinomiya, Japan

[73] Assignee: Albert Einstein College of Medicine of Yeshiva University, a Division of Yeshiva Universtiy, Bronx, N.Y.

[21] Appl. No.: 390,881

[22] Filed: Feb. 17, 1995

Related U.S. Application Data

[63] Continuation-in-part of Ser. No. 93,528, Jul. 19, 1993, abandoned.

[51] Int. Cl.$^6$ .............. C12N 5/02; C12N 5/06; A61K 31/66; C07F 9/02
[52] U.S. Cl. .......... 514/102; 514/106; 514/134; 558/155; 558/156; 435/375; 435/384
[58] Field of Search .............. 435/240.2; 514/102, 514/106, 134; 558/155, 156

[56] References Cited

PUBLICATIONS

Cuthbert, J.A. et al., FASEB Journal, vol. 4(7), p. A1747, abs. #309 1990.
Chakrabarti, R. et al., The Journal of Biological Chemistry, vol. 266(19), pp. 12216–12222 1991.
Tanaka, Y. et al., Nature, vol. 375(6527), pp. 155–158 May 1995.
Burk, M.R. et al., Eur. J. Immunol., vol. 25(7), pp. 2052–2058 1995.
Morita, C.T. et al., Immunity, vol. 3(4), pp. 495–507 Oct. 1995.

*Primary Examiner*—Michael G. Wityshyn
*Assistant Examiner*—Kristin Larson
*Attorney, Agent, or Firm*—Amster, Rothstein & Ebenstein

[57] ABSTRACT

This invention is directed to a method for stimulating the proliferation of Vγ2Vδ2 T cells comprising contacting Vγ2Vδ2 T cells with a Vγ2Vδ2 T cell proliferation stimulating amount of a compound selected from the group consisting of a monoalkyl phosphate and an alkenyl pyrophosphate.

15 Claims, 17 Drawing Sheets

METHOD FOR PROLIFERATING Vγ2Vδ2 T CELLS

STATEMENT OF GOVERNMENT INTEREST

This application is a continuation-in-part of application Ser. No. 08/093,528, filed Jul. 19, 1993, now abandoned the contents of which is incorporated by reference herein.

This invention was made with government support under Grant No. NIH AI07118. As such, the government has certain rights in this invention.

BACKGROUND OF THE INVENTION

T cells are thymus-derived cells in the immune system which mediate cellular immune reactions and regulate immune response. T lymphocytes (T cells) are divided into two subgroups by their usage of T cell receptors. About 90–98% of T cells have αβ receptors (αβ T cells) which recognize antigenic peptides bound to major histocompatibility complex I or II molecules. About 2–10% of T cells have γδ receptors (γδ T cells).

A major human γδ T cell subset expressing Vγ2 and Vδ2 germlines (i.e. Vγ2Vδ2 T cells) is found in human mycobacterial lesions (Modlin, R. L., et al. *Nature* 339:544–548 (1989)). Vγ2Vδ2 T cells have been shown to expand acutely in response to mycobacterial pathogens such as *M. tuberculosis* and *M. luprae*, bacterial pathogens such as Gram-positive and Gram-negative bacteria, as well as parasites such as *Plasmodium vivax* (Kabelitz, D., et al. *J. Exp. Med.* 171:667–679 (1990); Panchamoorthy, G., et al. *J. Immunol.* 147:3360–3369 (1991); De Libero, G., et al. *J. Exp. Med.* 173:1311–1322 (1991); Hara, T., et al. *J. Clin. Invest.* 90:204–210 (1992); Goerlich, R., et al. *Eur. J. Immunol.* 21:2613–2616 (1991); and Goodier, M., et al. *Int. Immunol.* 4:33–41 (1992)). In addition, certain hematopoietic tumor cell lines such as Daudi and RPMI 8226 are specifically recognized and lysed by Vγ2Vδ2 T cells (Fisch, P., et al. *Science* 250:1269–1273 (1990); Selin, L. K., et al. *Scand. J. Immunol.* 36:107–117 (1992)).

Because Vγ2Vδ2 T cells recognize antigens which are expressed by a variety of diseases in humans, there exists a need to selectively stimulate the proliferation of Vγ2Vδ2 T cells to enhance the immune response against these diseases. The present invention satisfies this need.

SUMMARY OF THE INVENTION

The present invention provides a method for stimulating the proliferation of Vγ2Vδ2 T cells comprising contacting Vγ2Vδ2 T cells with a Vγ2Vδ2 T cell proliferation stimulating amount of a compound selected from the group consisting of a monoalkyl phosphate, a hydroxy monoalkyl phosphate, a carboxy monoalkyl phosphate, a monoalkyl pyrophosphate, an alkenyl pyrophosphate, a γ-monoalkyl nucleoside triphosphate, a γ-monoalkyl deoxnucleoside triphosphate, a γ-alkenyl nucleoside triphosphate, and a γ-alkenyl deoxynucleoside triphosphate.

The method of the present invention may be used for enhancing the immune response against a variety of diseases which express antigens recognized by Vγ2Vδ2 T cells. By stimulating the proliferation of Vγ2Vδ2 T cells, it is believed that an enhanced immune response will be generated against the diseases which express antigens recognized by Vγ2Vδ2 T cells, thereby effectively treating the disease.

BRIEF DESCRIPTION OF THE FIGURES

FIG. 1A depicts the proliferation of the γδ T cell clone DG.SF68, which expresses Vγ2Vδ2, when cultured with crude reaction mixtures of the following alkyl phosphates: methyl phosphate (solid square), monoethyl phosphate (solid circle), n-propyl phosphate (solid triangle), n-butyl phosphate (solid diamond), amyl phosphate (open square), isopropyl phosphate (open circle), isoamyl phosphate (open triangle), and secbutyl phosphate (open diamond). FIG. 1B depicts the selective stimulation of γδ T cell clone SD9 by monoethyl phosphate (MEP, solid square), diethyl phosphate (DEP, solid circle), and triethyl phosphate (TEP, solid triangle). FIG. 1C depicts the stimulation of the γδ T cell clone SD9 by monoethyl phosphate (MEP, solid square), its hydroxyl derivative (β-hydroxyethyl phosphate, open circle), and its carboxyl derivative (phosphoglycolic acid, open triangle). The percentage of the maximal proliferation is shown.

FIG. 2A depicts the expansion by MEP of γδ T cells in primary cultures of PBMC as determined by two-color FACS analysis. The increase of γδ T cells by MEP is comparable to that stimulated by *M. tuberculosis* (M.tb) lysates. FIG. 2B depicts the two-color FACS analysis showing that γδ T cells expanded in primary culture by MEP exclusively expressed Vδ2. The percentages in the quadrants of interest are shown.

FIG. 3A shows the proliferation in response to MEP was restricted to γδ T cell clones expressing the Vγ2/Vδ2 receptor. The stimulation indices for the response to phytohemagglutinin (positive control) were greater than 6 for all clones, with a mean value of 47.3. FIG. 3B shows the cytolytic activity of primary γδ T cells expanded by MEP on tumor cell lines K562 and Daudi, with 30 μM MEP for 7 days (solid circle), with 30 μM MEP for days on cell lines depleted of Vδ2 cells by BB3 antibody and magnetic beads (Dynal)(solid triangle), and medium only (solid square). E/T represents the effector to target ratio.

FIG. 4A depicts the elution patterns of *M. Smegmatis* bioactive preparations on anion-exchange column chromatography. Proliferative responses (solid circle) and absorbance (open circle). Arrows indicate the fractions where inorganic phosphate (Pi) and pyrophosphate (PPi) derived from mycobacterial preparation are detected by ESI-MS/MS analysis, respectively (data not shown). FIG. 4B depicts rechromatography of the partially purified *M. smegmatis* antigens on a Q SEPHAROSE HP column. Proliferative responses (solid circle) and absorbance (open circle). FIG. 4C shows that the *M. tuberculosis* antigens were eluted at the same fractions on Q SEPHAROSE HP column chromatography. Proliferative responses (solid circle) and absorbance (open circle).

FIG. 5A depicts the ESI-MS/MS analysis of the purified mycobacterial antigens containing phosphate residues. FIG. 5B depicts the daughter ion spectra of the 245 ion species derived from the purified mycobacterial antigens. FIG. 5C depicts the authentic daughter ion spectra of synthetic isopentenyl pyrophosphate. FIG. 5D depicts the proliferation of 12G12 in response to isoprene units coupled with pyrophosphate. Pyrophosphate derivatives exemplified are isopentenol (solid circle), dimethylallyl alcohol (open triangle), geraniol (solid triangle), farnesol (solid square), geranylgeraniol (open circle), and isoamyl alcohol (open square).

FIG. 6A depicts the stimulation by γ-monoethyl derivatives of: 2'-deoxythymidine triphosphate (2'-dTTP, solid circle); 2',3'-dideoxythymidine triphosphate (2',3'-ddTTP, solid triangle); 2'-deoxyuridine triphosphate (2'-dUTP, solid square); 2'-deoxythymidine diphosphate (2'-dUDP, open circle); and 2'-deoxythymidine monophosphate (2'-dUMP, open triangle). FIG. 6B depicts the stimulation by γ-monoethyl derivatives of: uridine triphosphate (UTP, solid circle); xanthosine triphosphate (XTP, solid triangle); inosine triphosphate (ITP, solid square); guanosine triphosphate (GTP, open circle); cytosine triphosphate (CTP, open triangle); and adenosine triphosphate (ATP, open square). FIG. 6C represents a schematic diagram of isoprenoid biosynthetic pathways, and the relationship between the intermediates and oncogene modifications.

DETAILED DESCRIPTION OF THE INVENTION

Figure 1A:
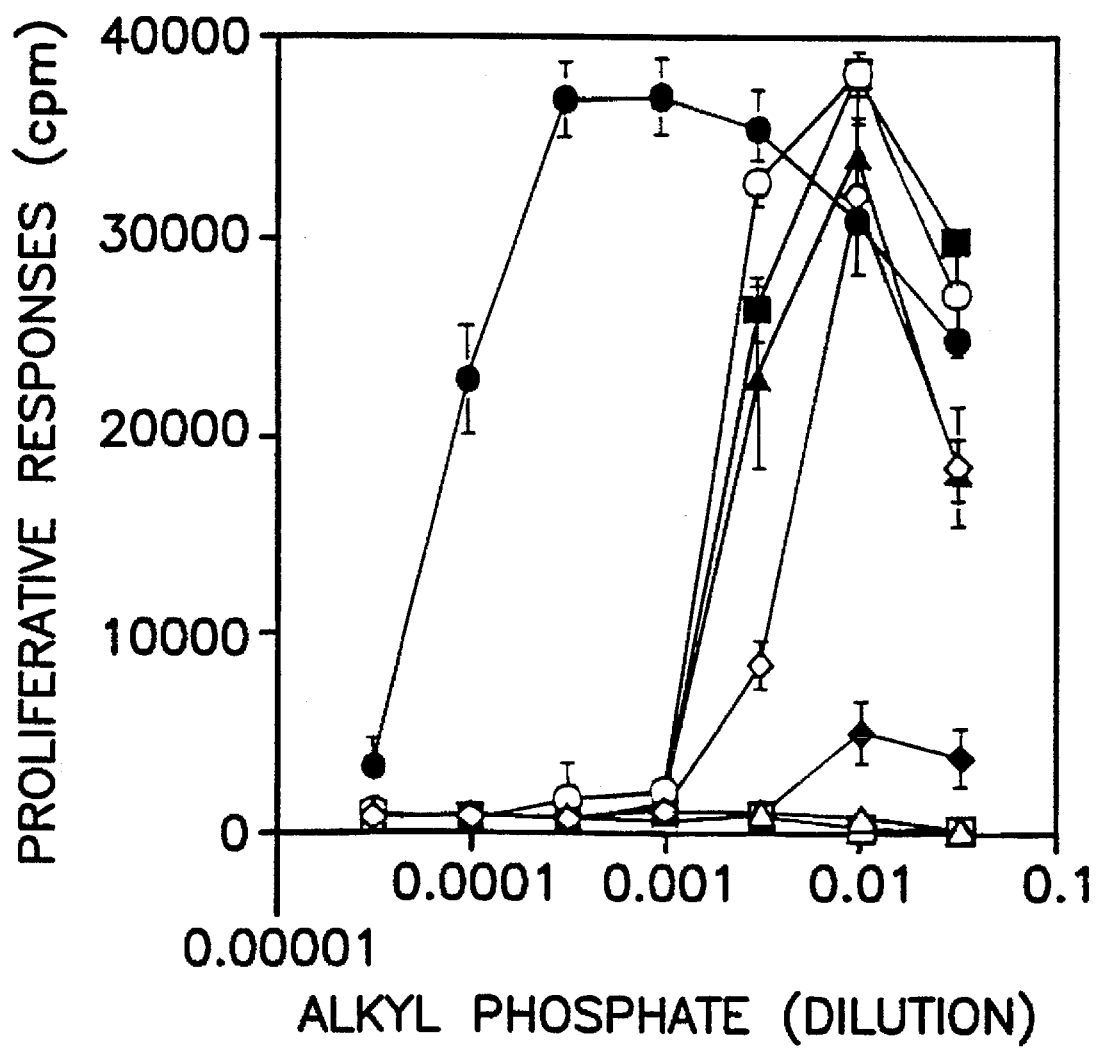
FIGS. 1A, 1B, and 1C depict γδ T cell response to monoalkyl phosphates.

The present invention provides a method for stimulating the proliferation of Vγ2Vδ2 T cells comprising contacting Vγ2Vδ2 T cells with a Vγ2Vδ2 T cell proliferation stimulating amount of a compound selected from the group consisting of a monoalkyl phosphate, a hydroxy monoalkyl phosphate, a carboxy monoalkyl phosphate, a monoalkyl pyrophosphate, an alkenyl pyrophosphate, a γ-monoalkyl nucleoside triphosphate, a γ-monoalkyl deoxnucleoside triphosphate, a γ-alkenyl nucleoside triphosphate, and a γ-alkenyl deoxynucleoside triphosphate.

The method of the present invention may be used for enhancing the immune response against a variety of diseases which express antigens recognized by Vγ2Vδ2 T cells. By stimulating the proliferation of Vγ2Vδ2 T cells, it is believed that an enhanced immune response will be generated against diseases which express antigens recognized by Vγ2Vδ2 T cells, thereby effectively treating the diseases. Specific diseases include but are not limited to leukemia, lymphoma, tuberculosis, leprosy, malaria, AIDS, rheumatoid arthritis, ulcerative colitis and anemia. A "Vγ2Vδ2 T cell proliferation stimulating amount" is an amount effective to induce the proliferation of said Vγ2Vδ2 T cells.

The "contacting" may be effected by administering to a subject in need of such immune enhancement a Vγ2Vδ2 T cell proliferation stimulating amount of one or more of the compounds above. Alternatively, biological fluid from the subject may be removed from the subject, treated with a Vγ2Vδ2 T cell proliferation stimulating amount of one or more of the compounds above, and reinfused back into the subject by standard techniques. "Biological fluid" includes but is not limited to sera, cerebrospinal fluid, synovial fluid, and preferably is sera. The subject may be any mammal, and is preferably a human or a cow.

The administration may be affected by means known to those skilled in the art such as oral, rectal, topical, intravenous, subcutaneous, intramuscular, or intraperitoneal routes of administration. The dosage form and amount can be readily established by reference to known chemotherapeutic treatments of the diseases. In general, however, the dosage of the compound will be within the range of about 0.01 μg/kg to about 100 mg/kg, and preferably between about 1 μg/kg and about 10 mg/kg. The actual dose will depend upon the route of administration, the pharmacokinetic properties of the individual treated, the disease being treated, as well as the results desired.

The compound may be formulated with one or more pharmaceutically acceptable diluents or carriers. The carrier must be "acceptable" in the sense of being compatible with the other ingredients of the formulation and not deleterious to the recipient thereof. Optionally, the compound may be administered with any other ingredients which may be therapeutic per se, and/or may be synergistic with the compounds of the present invention. These include chemotherapeutic agents known to act against the particular diseases. The concentration of the compound present in the formulation will depend upon the choice of carrier as well as the results desired.

Examples of suitable pharmaceutical carriers include lactose, sucrose, starch, talc, magnesium stearate, crystalline cellulose, methyl cellulose, carboxymethyl cellulose, glycerin, sodium alginate, gum arabic, powders, saline, water, among others. The choice of carrier will depend upon the route of administration. The formulations may conveniently be presented in unit dosage and may be prepared by methods well-known in the pharmaceutical art, by bringing the active compound into association with a carrier or diluent, as a suspension or solution, and optionally one or more accessory ingredients, e.g. buffers, flavoring agents, surface active agents, and the like.

For intravenous, intramuscular, subcutaneous, or intraperitoneal administration, the compound is combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

For oral administration, the formulation may be presented as capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

The monoalkyl phosphate useful in the method of the present invention has the formula $ROPO(OH)_2$ wherein R is a C1–C4 straight or branched chain alkyl, and may include but is not limited to monoalkyl phosphates selected from the group consisting of methyl phosphate, monoethyl phosphate, n-propyl phosphate, n-butyl phosphate and isopropyl phosphate. Preferably, the monoalkyl phosphate is monoethyl phosphate.

The hydroxy monoalkyl phosphate has the formula $HOROPO(OH)_2$ wherein R is a C1–C3 straight or branched chain alkyl, and may include but is not limited to hydroxy monoalkyl phosphates selected from the group consisting of hydroxy methyl phosphate, β-hydroxy ethyl phosphate, γ-hydroxy propyl phosphate and hydroxy isopropyl phosphate.

The carboxy monoalkyl phosphate has the formula HOOCROPO(OH)$_2$ wherein R is a C1–C2 straight or branched chain alkyl, and may include but is not limited to carboxy monoalkyl phosphates selected from the group consisting of phosphoglycolic acid and phosphopropionic acid. The alkenyl phosphate has the formula ROPO(OH)$_2$ wherein R is a C2–C20 straight or branched chain alkenyl, and may include but is not limited to alkenyl phosphates selected from the group consisting of allyl phosphate, crotyl phosphate, dimethylallyl phosphate, isopentenyl phosphate, geranyl phosphate, farnesyl phosphate, geranylgeranyl phosphate, 3-methyl-2-pentenyl phosphate, and 2-methyl-2-hexenyl phosphate. Preferably, the alkenyl phosphate is dimethylallyl phosphate.

The monoalkyl pyrophosphate has the formula ROPO(OH)OPO(OH)$_2$ wherein R is a C1–C4 straight or branched chain alkyl, and may include but is not limited to methyl pyrophosphate, monoethyl pyrophosphate, n-propyl pyrophosphate, n-butyl pyrophosphate and isopropyl pyrophosphate. Preferably, the monoalkyl pyrophosphate is ethyl pyrophosphate.

The alkenyl pyrophosphate has the formula ROPO(OH)OPO(OH)$_2$ wherein R is a C2–C20 straight or branched chain alkenyl, and may include but is not limited to allyl pyrophosphate, crotyl pyrophosphate, dimethylallyl pyrophosphate, isopentenyl pyrophosphate, geranyl pyrophosphate, farnesyl pyrophosphate, geranylgeranyl pyrophosphate, 3-methyl-2-pentenyl pyrophosphate, and 3-methyl-2-hexenyl pyrophosphate. Preferably, the alkenyl pyrophosphate is isopentenyl pyrophosphate or 3-methyl-2-hexenyl pyrophosphate.

The γ-monoalkyl nucleoside triphosphate or γ-monoalkyl nucleoside deoxynucleoside triphosphate each has the formula R-NTP or R-dNTP, respectively, wherein R is a C1–C4 straight or branched chain alkyl, N is a nucleoside selected from the group consisting of uridine, xanthosine, inosine, guanosine, cytosine, and adenosine, dN is a deoxynucleoside selected from the group consisting of 2'-deoxythymidine, 2',3'-dideoxythymidine, and 2'-deoxyuridine, and NP is triphosphate.

The γ-monoalkyl nucleoside triphoshates or γ-monoalkyl deoxynucleoside triphosphates may include but are not limited to:

methyl uridine-triphosphate, methyl xanthosine-triphosphate, methyl inosine-triphosphate, methyl guanosine-triphosphate, methyl cytosine-triphosphate, methyl adenosine-triphosphate, methyl 2'-deoxythymidine-triphosphate, methyl 2',3'-dideoxythymidine-triphosphate, and methyl 2'-deoxyuridine-triphosphate;

monoethyl uridine-triphosphate, monoethyl xanthosine-triphosphate, monoethyl inosine-triphosphate, monoethyl guanosine-triphosphate, monoethyl cytosine-triphosphate, monoethyl adenosine-triphosphate, monoethyl 2'-deoxythymidine-triphosphate, monoethyl 2',3'-dideoxythymidine-triphosphate, and monoethyl 2'-deoxyuridine-triphosphate;

n-propyl uridine-triphosphate, n-propyl xanthosine-triphosphate, n-propyl inosine-triphosphate, n-propyl guanosine-triphosphate, n-propyl cytosine-triphosphate, n-propyl adenosine-triphosphate, n-propyl 2'-deoxythymidine-triphosphate, n-propyl 2',3'-dideoxythymidine-triphosphate, and n-propyl 2'-deoxyuridine-triphosphate;

n-butyl uridine-triphosphate, n-butyl xanthosine-triphosphate, n-butyl inosine-triphosphate, n-butyl guanosine-triphosphate, n-butyl cytosine-triphosphate, n-butyl adenosine-triphosphate, n-butyl 2'-deoxythymidine-triphosphate, n-butyl 2',3'-dideoxythymidine-triphosphate, and n-butyl 2'-deoxyuridine-triphosphate; and isopropyl uridine-triphosphate, isopropyl xanthosine-triphosphate, isopropyl inosine-triphosphate, isopropyl guanosine-triphosphate, isopropyl cytosine-triphosphate, isopropyl adenosine-triphosphate, isopropyl 2'-deoxythymidine-triphosphate, isopropyl 2',3'-dideoxythymidine-triphosphate, and isopropyl 2'-deoxyuridine-triphosphate.

The γ-alkenyl nucleoside triphosphate or γ-alkenyl deoxynucleoside triphosphate each has the formula R-NTP or R-dNTP wherein R is a C2–C20 straight or branched chain alkenyl, N is a nucleoside selected from the group consisting of uridine, xanthosine, inosine, guanosine, cytosine, and adenosine, dN is a deoxynucleoside selected from the group consisting of 2'-deoxythymidine, 2',3'-dideoxythymidine, and 2'-deoxyuridine, and NP is triphosphate.

The γ-monoalkyl nucleoside triphoshates or γ-monoalkyl deoxynucleoside triphosphates may include but are not limited to:

allyl uridine-triphosphate, allyl xanthosine-triphosphate, allyl inosine-triphosphate, allyl guanosine-triphosphate, allyl cytosine-triphosphate, allyl adenosine-triphosphate, allyl 2'-deoxythymidine-triphosphate, allyl 2',3'-dideoxythymidine-triphosphate, and allyl 2'-deoxyuridine-triphosphate;

crotyl uridine-triphosphate, crotyl xanthosine-triphosphate, crotyl inosine-triphosphate, crotyl guanosine-triphosphate, crotyl cytosine-triphosphate, crotyl adenosine-triphosphate, crotyl 2'-deoxythymidine-triphosphate, crotyl 2',3'-dideoxythymidine-triphosphate, and crotyl 2'-deoxyuridine-triphosphate;

dimethylallyl uridine-triphosphate, dimethylallyl xanthosine-triphosphate, dimethylallyl inosine-triphosphate, dimethylallyl guanosine-triphosphate, dimethylallyl cytosine-triphosphate, dimethylallyl adenosine-triphosphate, dimethylallyl 2'-deoxythymidine-triphosphate, dimethylallyl 2',3'-dideoxythymidine-triphosphate, and dimethylallyl 2'-deoxyuridine-triphosphate;

isopentenyl uridine-triphosphate, isopentenyl xanthosine-triphosphate, isopentenylinosine-triphosphate, isopentenyl guanosine-triphosphate, isopentenyl cytosine-triphosphate, isopentenyl adenosine-triphosphate, isopentenyl 2'-deoxythymidine-triphosphate, isopentenyl 2',3'-dideoxythymidine-triphosphate, and isopentenyl 2'-deoxyuridine-triphosphate;

geranyl uridine-triphosphate, geranyl xanthosine-triphosphate, geranyl inosine-triphosphate, geranyl guanosine-triphosphate, geranyl cytosine-triphosphate, geranyl adenosine-triphosphate, geranyl 2'-deoxythymidine-triphosphate, geranyl 2',3'-dideoxythymidine-triphosphate, and geranyl 2'-deoxyuridine-triphosphate;

farnesyl uridine-triphosphate, farnesyl xanthosine-triphosphate, farnesyl inosine-triphosphate, farnesyl guanosine-triphosphate, farnesyl cytosine-triphosphate, farnesyl adenosine-triphosphate, farnesyl 2'-deoxythymidine-triphosphate, farnesyl 2',3'-dideoxythymidine-triphosphate, and farneysl 2'-deoxyuridine-triphosphate;

geranylgeranyl uridine-triphosphate, geranylgeranyl xanthosine-triphosphate, geranylgeranyl inosine-triphosphate, geranylgeranyl guanosine-triphosphate, geranylgeranyl cytosine-triphosphate, geranylgeranyl adenosine-triphosphate, geranylgeranyl 2'-deoxythymidine-triphosphate, geranylgeranyl 2',3'-dideoxythymidine-triphosphate, and geranylgeranyl 2'-deoxyuridine-triphosphate;

3-methyl-2-pentenyl uridine-triphosphate, 3-methyl-2-pentenyl xanthosine-triphosphate, 3-methyl-2-pentenyl inosine-triphosphate, 3-methyl-2-pentenyl guanosine-triphosphate, 3-methyl-2-pentenyl cytosine-triphosphate, 3-methyl-2-pentenyl adenosine-triphosphate, 3-methyl-2-pentenyl 2'-deoxythymidine-triphosphate, 3-methyl-2-pentenyl 2',3'-dideoxythymidine-triphosphate, and 3-methyl-2-pentenyl 2'-deoxyuridine-triphosphate; and 2-methyl-2-hexenyl uridine-triphosphate, 2-methyl-2-hexenyl xanthosine-triphosphate, 2-methyl-2-hexenyl inosine-triphosphate, 2-methyl-2-hexenyl guanosine-triphosphate, 2-methyl-2-hexenyl cytosine-triphosphate, 2-methyl-2-hexenyl adenosine-triphosphate, 2-methyl-2-hexenyl 2'-deoxythymidine-triphosphate, 2-methyl-2-hexenyl 2',3'-dideoxythymidine-triphosphate, and 2-methyl-2-hexenyl 2'-deoxyuridine-triphosphate.

The present invention is described in the following Experimental Details Section which is set forth to aid in the understanding of the invention, and should not be construed to limit in any way the invention as defined in the claims which follow thereafter.

Experimental Details Section

I. Monoalkylphosphates

Preparation of Monoalkylphosphates. Alkyl phosphates were prepared by reacting 1 gram of phosphorus pentoxide (Fluka) with 1 ml of the appropriate alcohol (provided below), as described in Kosolapoff, et al. *Organophosphorous Compounds,* John Wiley & Sons, New York, pp. 220–277 (1950). The reaction was carried out by heating at 65° C. for 9 hours. 0.2 ml of water was added at 7 hours of the reaction. To obtain the purified alkyl phosphate, the reaction mixture was applied to an anion exchange HPLC (Dionex) using sodium hydroxide and sodium acetate as eluates. The eluted fraction was desalted by gel filtration chromatography using a BIOGEL P2 column (Biolad). To verify the identity of the compound, fast atom bombardment mass spectral analyses were performed on a Finnigran MAT-90 mass spectrometer (FAB-MS) in the negative ion mode. Diethyl phosphate (DEP) and triethyl phosphate (TEP) were purchased from KODAK and Aldrich, respectively. β-hydroxyethyl-phosphate was prepared from ethylene oxide by the action of aqueous disodium hydrogen phosphate as described in Kosolapoff, et al., supra, and purified by anion-exchange chromatography (QAE-A25, Pharmacia). Phosphoglycolic was purchased from Sigma. The alkyl phosphates also may be synthesized using the procedures described in Popjak, G., et al. *J. Biol. Chem.* 237:56–61 (1962). The Popjak, G., et al. procedures are preferred.

Derivation/Maintenance of T Cell Clones. All T cell clones were derived by limiting dilution. DG clones were derived from the synovial fluid of a rheumatoid arthritis patient by stimulation with *M. tuberculosis.* The 12G12 γδ T cell clone was derived from *M. tuberculosis* H37Ra-stimulated Ficoll/Hypaque-purified peripheral blood mononuclear cells (PBMC) of a patient with tuberculoid leprosy. γδ clones SD9, 10E12, 4H1, SE3, S58, PS7, 4B6, 24B1, 5C, JF1, and αβ T cell clones were derived from *M. tuberculosis* stimulated PBMC of a normal donor. γδ T clones, HF.2, HD.109, CP.2B2, HF.15, and HF.41 were derived from PMBC with phytohemagglutinin (PHA) (Morita, C. T., et al. *Eur. J. Immunol.* 21:2999–3007 (1991); Spits, H., et al. *J. Immunol.* 147:1180–1188 (1991)), and γδ T clones, T7A5, T7C6, T7C7, T5B9, MD16, MD21, MD22, and MD26 were similarly derived (Casorati, G., et al. *J. Exp. Med.* 170:1521–1535 (1989)).

Proliferation and Cytotoxic Assays. Assays were performed in triplicate using 4–10×10$^4$ γδ or αβ T cells plus 5–10×10$^4$ irradiated allogenic PBMC per flat or round bottom well of a 96-well plate. *M. tuberculosis* antigen was prepared by suspending 100 mg of heat killed H37Ra (Difco) with 10 ml of distilled water followed by sonication. For some experiments, crude reaction mixtures of alkyl phosphates were diluted to 1:200 for use. After 24–42 hours, the cells were pulsed with [$^3$H] thymidine (1 μCi/well; 1 Ci=37 GBq), harvested at 48 hours, and counted by liquid scintillation. For cytotoxicity assays, primary lymphocytes expanded for 7 days with MEP (30 μM) were added to Daudi or K562 cells (2×10$^3$) labeled for 90 min with 100 μCi of $^{51}$Cr, and chromium release was measured at 6 h.

MEP-Induced Expansion and Flow Cytometric Analysis of γδ T cells. PBMC from healthy donors were cultured at 1.2×10$^6$ ml in Yssel's medium together with 30 μM MEP or *M. tuberculosis* lysate (1:30 dilution). On day 7, viable cells were separated by Ficoll-Hypaque and then stained with antibodies and analyzed. Antibodies used included: phycoerythrin-conjugated anti-TCR γ/δ-1, fluorescein isothiocyanate-conjugated anti-CD3 (Becton Dickinson), anti-Vδ2 chain (BB3), anti-Vγ2 chain, and fluorescein isothiocyanate-conjugated-anti-mouse IgG antibody (Ortho Diagnostics System Laboratories, Webster, Tex.). Stained cells were analyzed on a FACSCAN analyzer (Becton Dickinson). Controls with isotype-matched antibodies established the quadrants such that over 99% of cells are in the double-negative region.

Figure 1B:
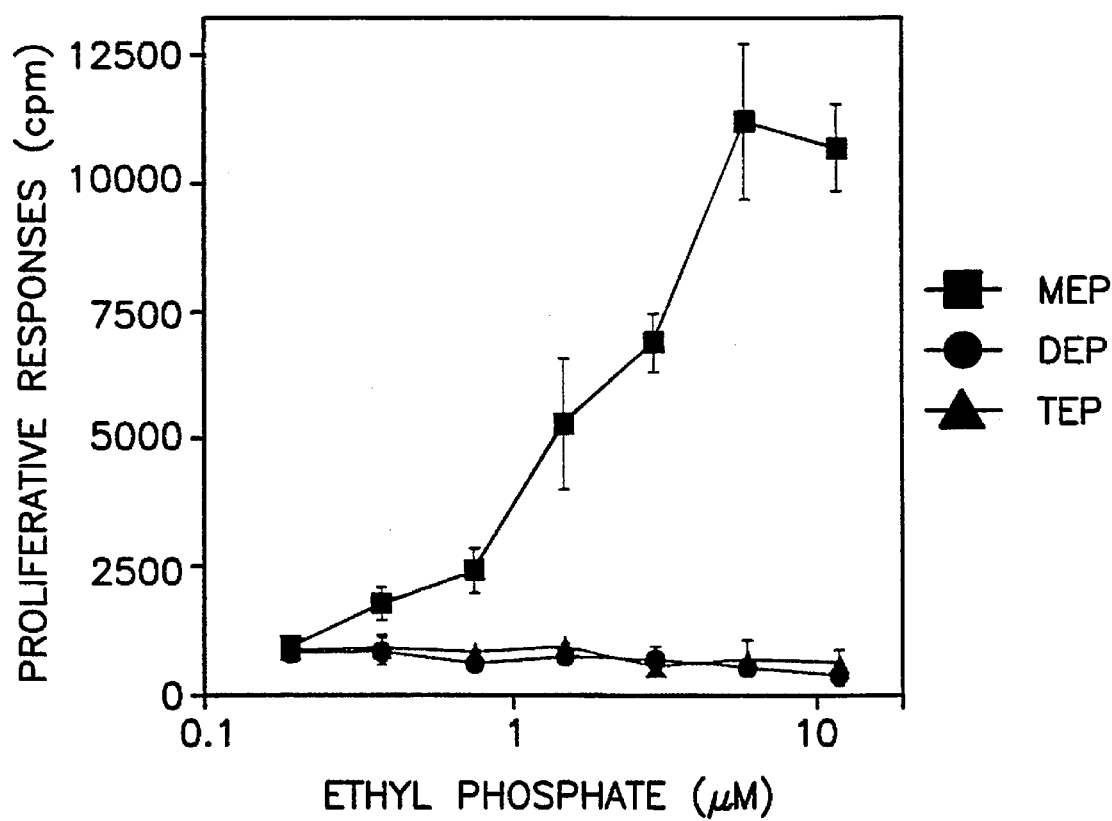
Figure 1C:
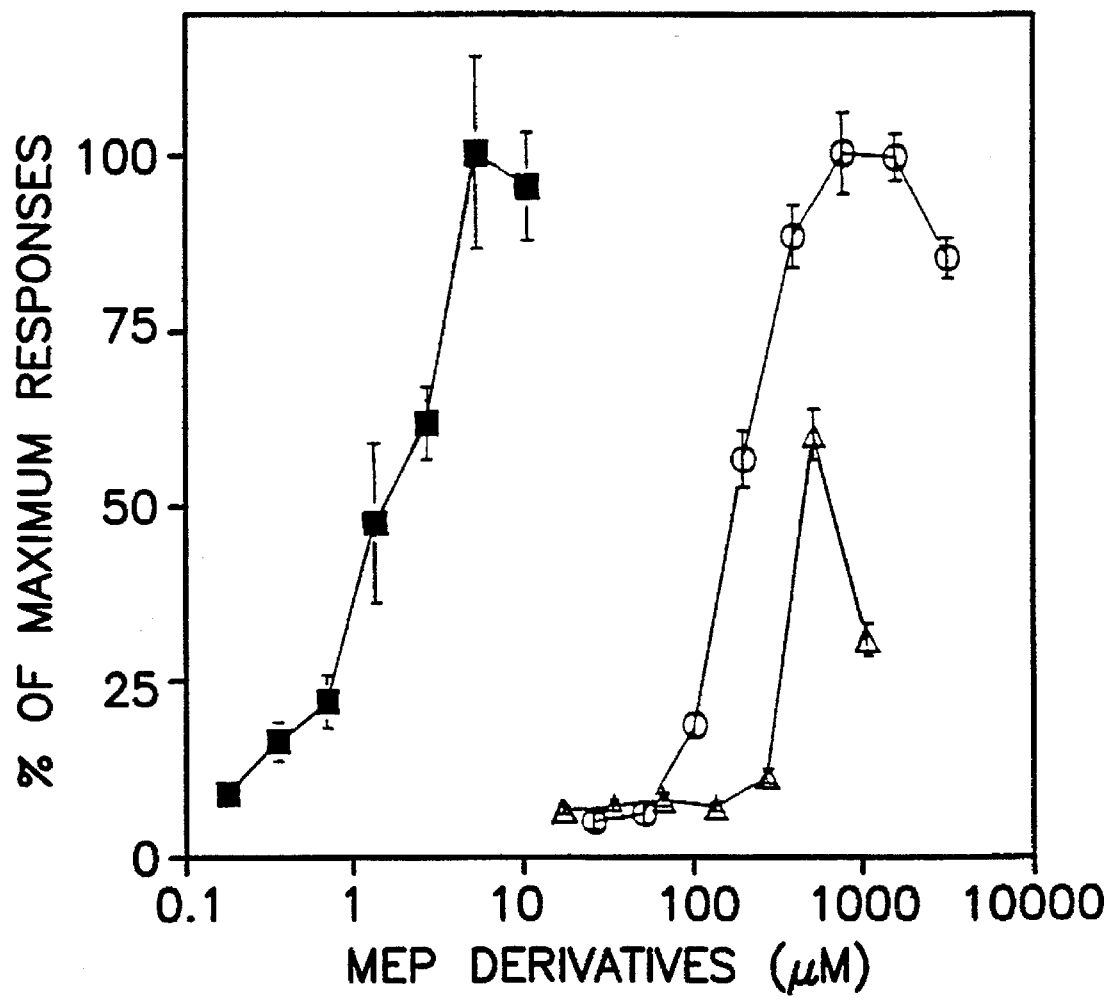

MEP and Other Monoalkyl Phosphates Stimulate γδ T Cells. Various alkyl phosphates were tested for their ability to stimulate the proliferation of the γδ T cell clone, DG.SF68, which expresses Vγ2Vδ2. The results are presented in FIG. 1A. All alkyl phosphates tested with four or fewer carbons induced proliferation. One compound, MEP, was 50- to 100-fold more bioactive than the other compounds. γδ T cell clones proliferated in a dose-dependent manner to HPLC-purified MEP, reaching half maximal proliferation at 2 μM, but failed to proliferate when exposed to the diethyl or triethyl derivatives (see FIG. 1B). Neither αβ T-cell clones (FIG. 3A) nor NK clones (data not shown) proliferated in response to MEP. Modification of C-2 by addition of a hydroxy group or by conversion to a carboxyl group reduced the specific activity of MEP by 100- to 200-fold (see FIG. 1C), whereas the addition of an amino group totally abolished biological activity (data not shown). Common three-carbon metabolites such as β-glycerophosphate, 2-phosphoglycerate, 3-phosphoglycerate, and phosphoenolpyruvate were also inactive (data not shown).

Figure 2A:
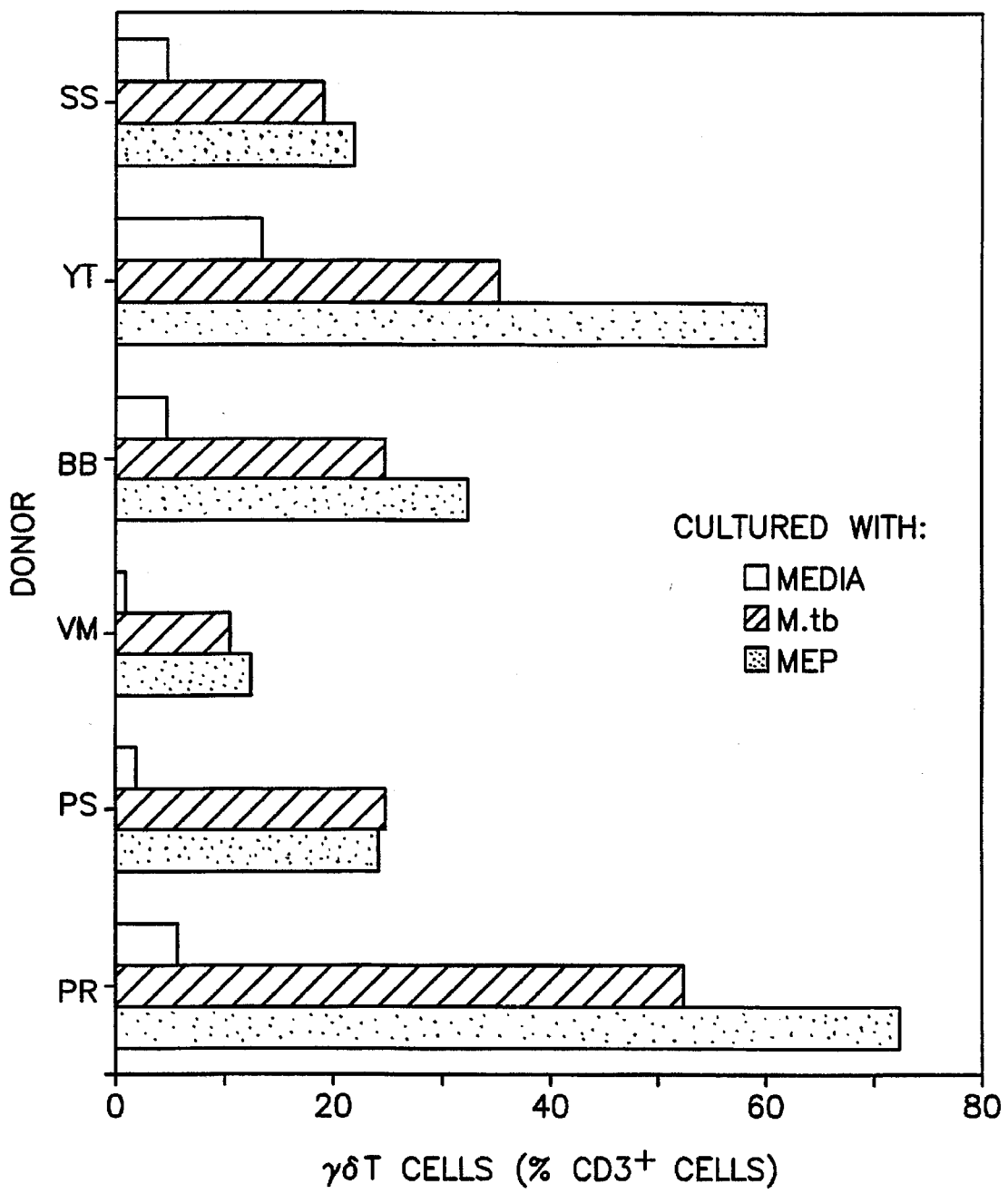
FIGS. 2A and 2B depict the effect of MEP on primary PBMC and the specificity in the response of γδ T cells to monoalkyl phosphate ligands.

MEP Selectively Activates the Vγ2/Vδ2+ Subset of γδ T cell Cells Through Cognate TCR Recognition. Previously, it has been shown that ligand(s) of *M. tuberculosis* and other mycobacterial species predominantly induce the expansion of γδ T cells from primary cultures of freshly isolated PBMC (Modlin, R. L., et al. *Nature (London)* 339:544–548 (1989); Kabelitz, D., et al. *J. Exp. Med.* 171:667–679 (1990); Panchamoorthy, G., et al. *J. Immunol.* 147:3360–3369 (1991); De Libero, G., et al. *J. Exp. Med.* 173:1311–1322 (1991); and Hacker, G., et al. *Infect. Immun.* 60:2753–2757 (1992)). A similar selective expansion of γδ T cells was observed after a 7 day period of exposure of PBMC from all healthy donors tested (12 individuals) to MEP (FIG. 2A).

Figure 2B:
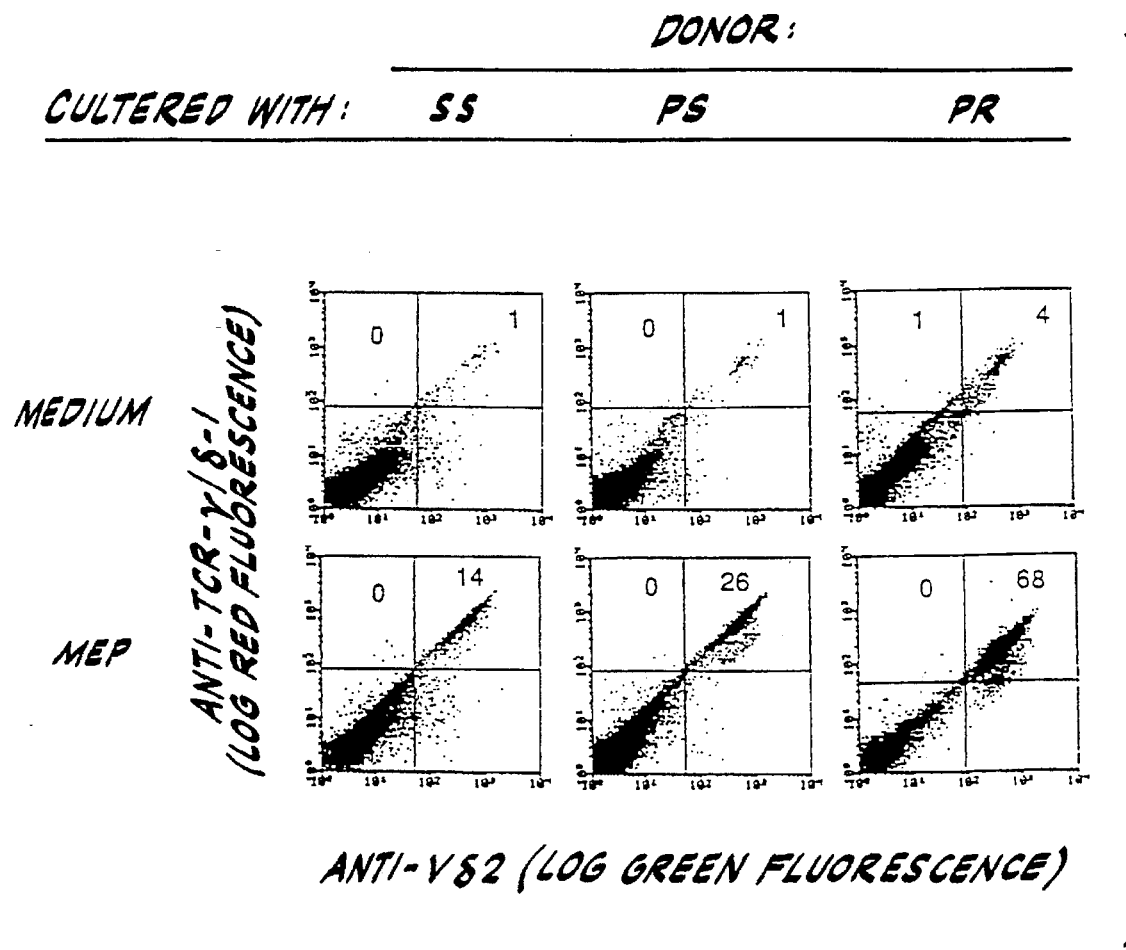

To determine if MEP expands the same Vγ2/Vδ2$^+$ subset of γδ T cells that is stimulated by mycobacteria, primary γδ T cells from normal individuals were expanded by MEP, and their V gene expression was determined by two-color fluorescence-activated cell sorting (FACS) analysis. The expanded γδ T cell population was restricted to those that expressed the Vδ2 gene (FIG. 2B); no expansion of Vδ1— expressing γδ T cells was detected.

Figure 3A:
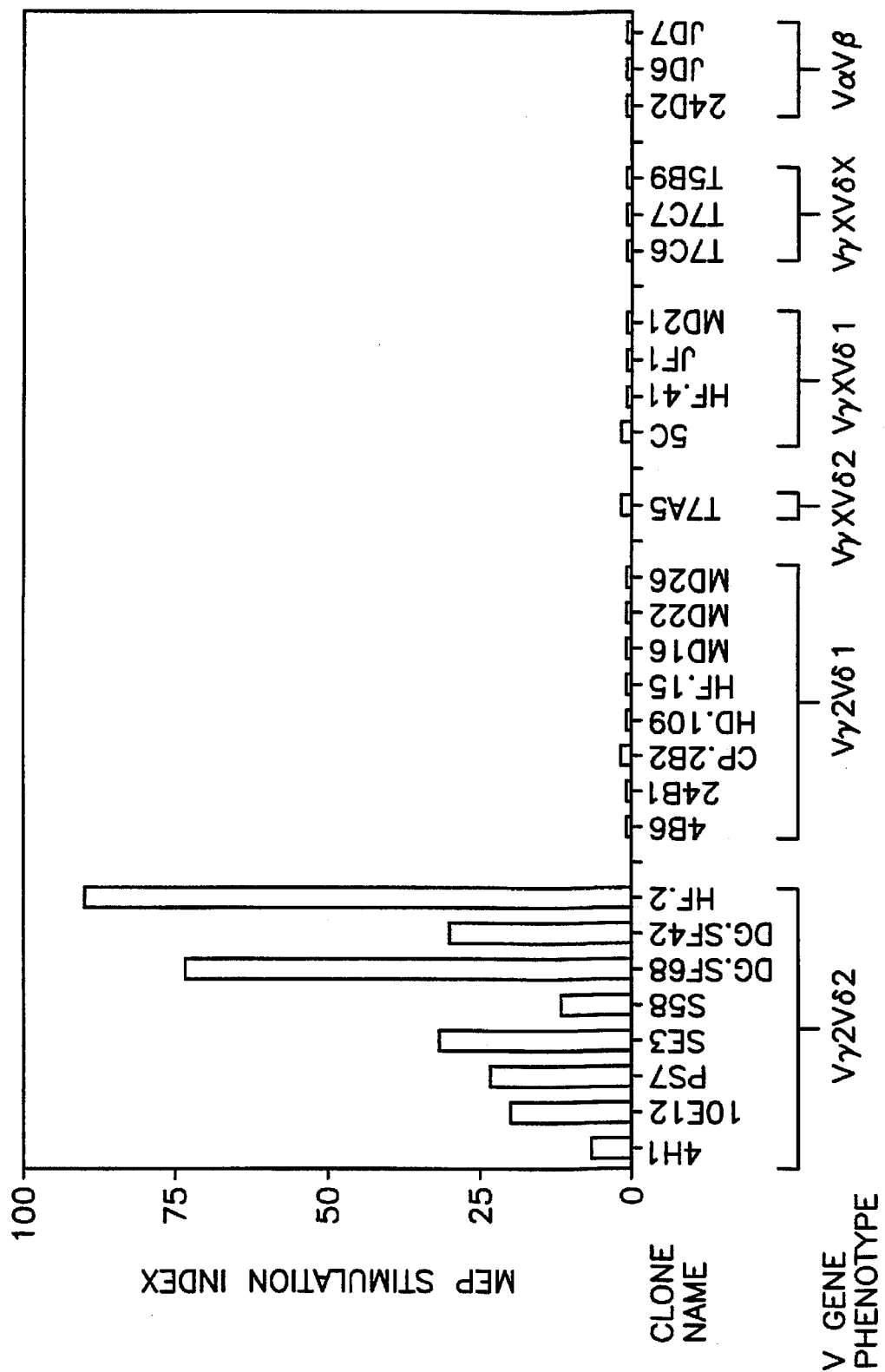
FIGS. 3A and 3B depict the effect of MEP on γδ T cell clones and heterogeneity in the response of Vγ2/Vδ2$^+$ T cell clones to monoalkyl phosphate ligands.

To define the V gene requirement for activation further, a panel of γδ T cell clones expressing a variety of γ and δ V genes was screened for proliferation to MEP. Strikingly, responsiveness to MEP was restricted to clones expressing Vγ2 in conjunction with Vδ2 (FIG. 3A). Clones expressing Vγ2 paired with Vδ1 or clones expressing Vδ2 paired with Vγ genes other than Vγ2 were not reactive to either MEP (FIG. 3A) or *M. tuberculosis* lysates (data not shown).

The proliferation of γδ T cell clones to MEP was abolished by inclusion of anti-TCR-δ antibodies (Table 1 below), which, together with the V gene specificity, suggests that the γδ TCR is directly involved in the recognition of MEP.

TABLE 1

The Monoethyl Phosphate (MEP) Response is Blocked by Antibody to the Gamma Delta T Cell Receptor (TCR)

| | | Proliferative Responses (cpm) | |
|---|---|---|---|
| MEP | Antibody | SD9 | 12G12 |
| − | None | 1075 | 151 |
| + | None | 9955 | 4578 |
| + | Control mouse IgG | 9801 | 4760 |
| + | Anti-MHC Class I | 6827 | 3782 |
| + | Anti-MHC Class II | 10187 | 5347 |
| + | Anti-TCR (Vδ2) | 929 | 95 |

γδ clones SD9 and 12G12 were stimulated with monoethyl phosphate (MEP) (30 μM) in the absence of antigen-presenting cells and in the presence of the indicated antibody. Antibodies used were mouse IgG1 plus IgG2a (2 μg/ml, Zymed) as a control, anti-HLA-A, B, C, E (W6/32, 1:1000; Sera-Lab. Crawley Down, Sussex, U.K.), anti-HLA-DR (MID3, 2 ug/ml; Sera-Lab), and anti-Vδ2 (BB3, 1:2000). All antibodies were dialyzed to remove sodium azide before assay. The proliferative responses to MEP in the presence of irradiated allogeneic PBMC was 947 (−MEP) and 10430 (+MEP) for SD9, and 204 (−MEP) and 6841 (+MEP) for 12G12. Results shown are representative of three separate experiments, and are means of triplicate values, with standard errors of less than 10%.

Figure 3B:
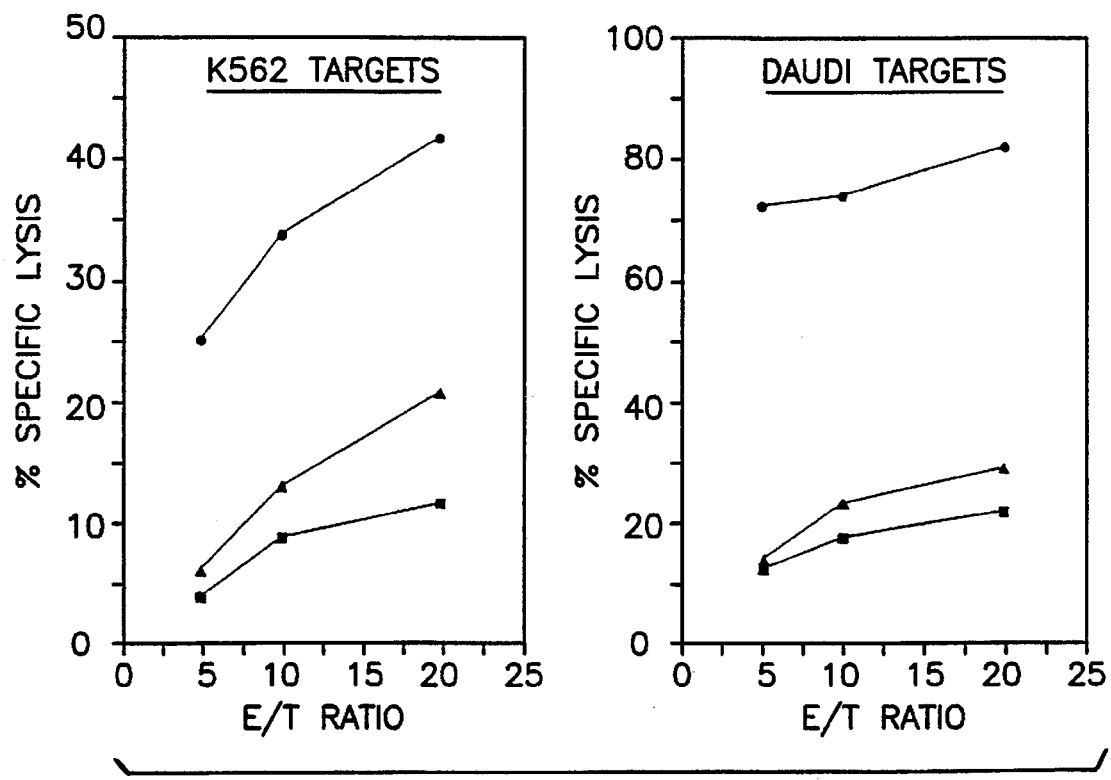

Vγ2/Vδ2-Bearing T Cells Expanded in Culture by Monoalkyl Phosphate Lyse Tumor Cells. As shown in FIG. 3B, MEP-stimulated Vγ2/Vδ2-bearing T cells have the capacity to lyse human transformed hematopoietic cells as illustrated for Daudi and K562 cells. Thus, monoalkyl phosphate compounds appear to act as antigens or superantigens that stimulate Vγ2/Vδ2-bearing T cells through their TCR in a manner similar to that of mycobacterial ligands. Monoalkyl Phosphate Expands γδ T cells in Culture of HIV Infected Peripheral Blood. The expansion of γδ T cells from primary in vitro culture of peripheral blood cells of three healthy individuals and one HIV positive individual by monoethyl phosphate was examined, and the results are presented in Table 2 below. γδ T cells in peripheral blood ranged from 2–10% of T cells. However, when cultivated in vitro with monoethyl phosphate, they greatly increased in number up to 72%. Surprisingly, the effect of monoethyl phosphate was obtained on peripheral γδ T cells which did not have the CD4 molecule, which is the receptor for HIV. γδ T cells remained sensitive to monoethyl phosphate in AIDS patients and may therefore functionally compensate for the loss of CD4+ αβ T cells that undergo decrease in number or paralysis from HIV infection. Increasing γδ T cells from all of the subjects were of Vδ positive subset and of CD4−CD8−.

TABLE 2

| | γδ T Cells (% T Cells) | |
|---|---|---|
| DONOR | CONTROL | MONOETHYL PHOSPHATE |
| B.B.[1] | 5 | 35 |
| P.S.[1] | 2 | 33 |
| P.R.[1] | 8 | 72 |
| A.B.[2] | 4 | 42 |

[1]Healthy donors whose ages range from 35 to 53.
[2]An AIDS patient of 32 years old who has been treated with AZT for 9 months and whose CD4/8 ratio was 0.85.

II. Purification of Natural Mycobacterial Antigens

Mycobacteria *M. smegmatis* was cultured in Middlebrook 7H9 broth (Difco) with 0.5% glycerol and 0.05% TWEEN 80 at 37° C. for 2 days, and the culture filtrate was applied to charcoal-Celite column chromatography (2.5×1.5 cm, Fisher). The mycobacteria were again cultured in the clear eluate supplemented with 7H9, glycerol and TWEEN 80 under the same condition. This procedure was repeated 9 times and 7 million units were obtained. One unit is defined as the antigen concentration required for half-maximal proliferative responses of γδ T cell clone 12G12, derived from the lymphocytes of a tuberculoid leprosy patient. To the solution, 5 volumes of methanol were added, and the clear supernatant was evaporated to dryness under the reduced pressure at room temperature. The residue was rehydrated in 1 L $H_2O$ and passed through a collodion membrane (Schleicher-Schuell).

Figure 4A:
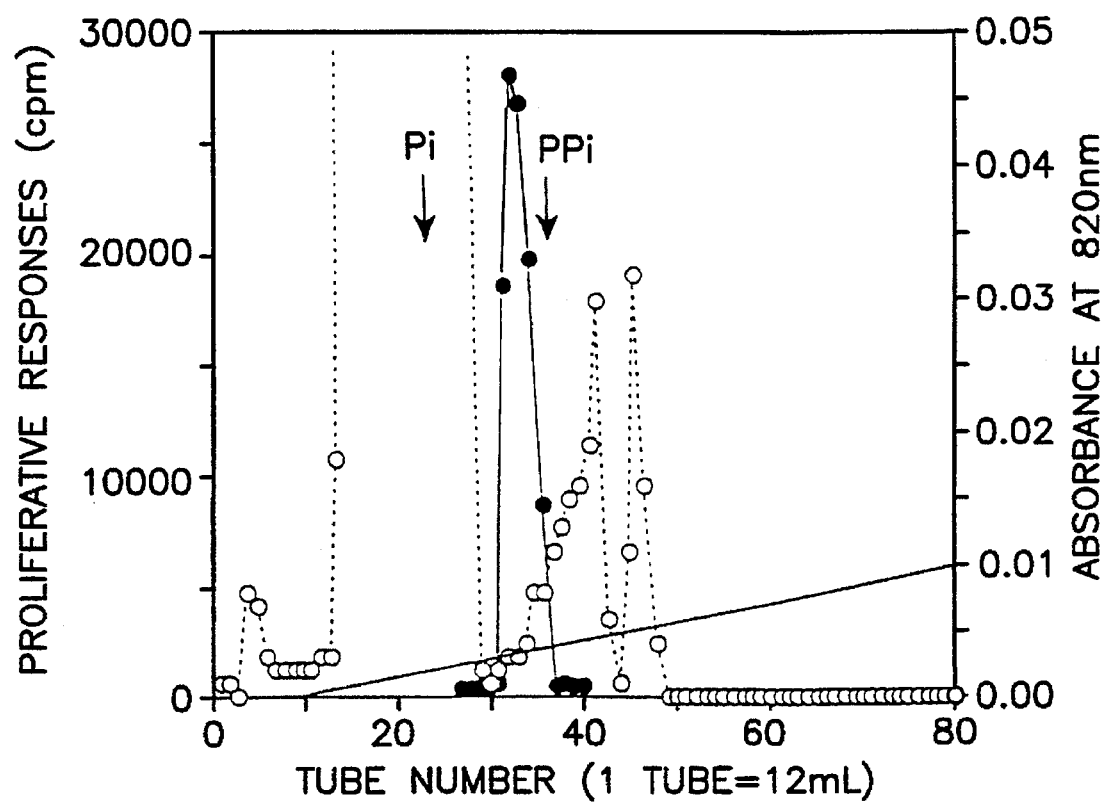
FIGS. 4A, 4B, and 4C depict the purification of natural mycobacterial antigens.
Figure 4B:
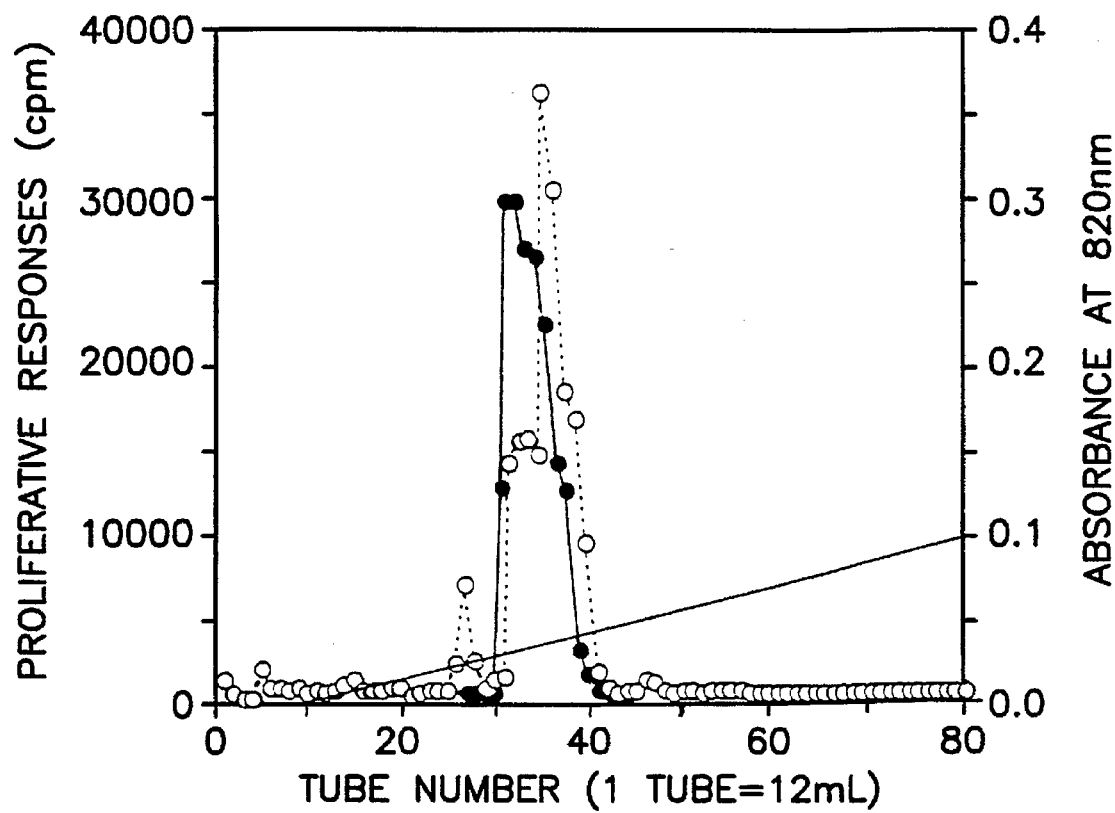
Figure 4C:
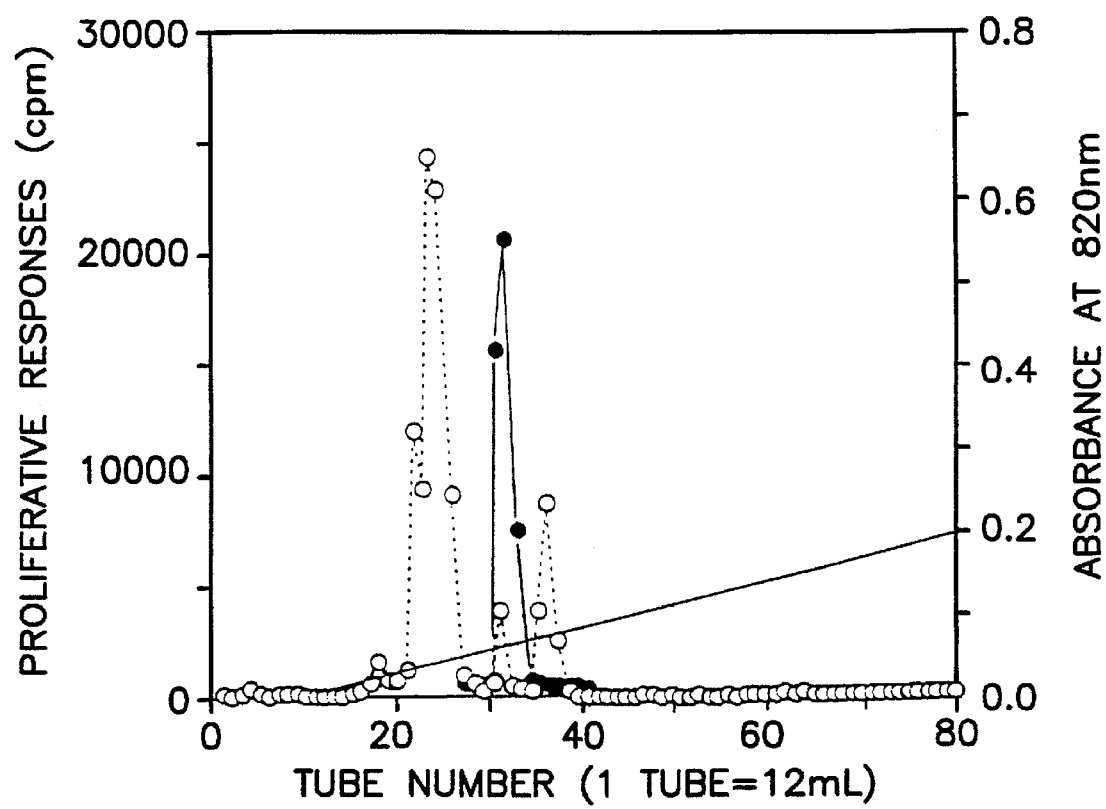

The filtrate was aliquoted to 40 portions and applied to Q SEPHAROSE HP column chromatography (2.5×8 cm) with 0–500 mM triethylammonium bicarbonate buffer, pH 7.5, respectively. Active fractions from 40 column chromatography runs as described in the description to FIG. 4A were combined and applied to cellulose (Sigma) flash column chromatography with isopropanol:conc. $NH_4OH:H_2O$ (7:2:1, v/v/v) to remove nucleotide contaminants, then the active fractions were rechromatographed by Q Sepharose HP (2.5×8 cm). *M. tuberculosis* H37Ra (0.6 g, Difco) ligands were extracted with $H_2O$ by sonication in a water bath overnight at 4° C. and applied to charcoal-Celite column chromatography (2.5×1.5 cm).

The eluate was passed through a collodion membrane and applied to Q SEPHAROSE HP column chromatography (2.5×8 cm) with 0–500mM triethylammonium bicarbonate buffer, pH 7.5. For phosphate assay (Ames, B. N. *Methods Enzymol.* 8:115–118 (1966)), 10 μL samples were used in FIGS. 5A, 5B, and 5C, and 0.5, 0.01 or 2 μL samples were used for the proliferation assay, respectively. Proliferation assays were performed in triplicate using $5 \times 10^4$ cloned γδ T cells per round bottom well of a 96-well plate. After 36 hours, the cells were pulsed with [methyl-$^3$H] thymidine (1 μCi/well), harvested at 48 hours, and counted by liquid scintillation.

Mass spectral analysis was performed on a API-III triple-quadrupole mass spectrometer (PE-SCIEX, Ontario, Canada) using the SCIEX-IonSpray interface with nitrogen as the nebulizer gas. Flow injection analysis using 100% methanol plus 0.1% trifluoroacetic acid at 10 μL/min was used to introduce the samples into the mass spectrometer. Collisional activated dissociation (CAD) was performed using argon as the collision gas at a collision gas thickness of $1.7 \times 10^{10}$ molecules/cm$^2$ and a collision energy of 30 eV. Under these CAD conditions, parent ion scans of 79 amu and daughter ion spectra of the selected parent ion, m/z 245, were obtained. Samples were diluted 1:50 using 0.2% $NH_4OH$ and 10 μL aliquot was injected.

Figure 5A:
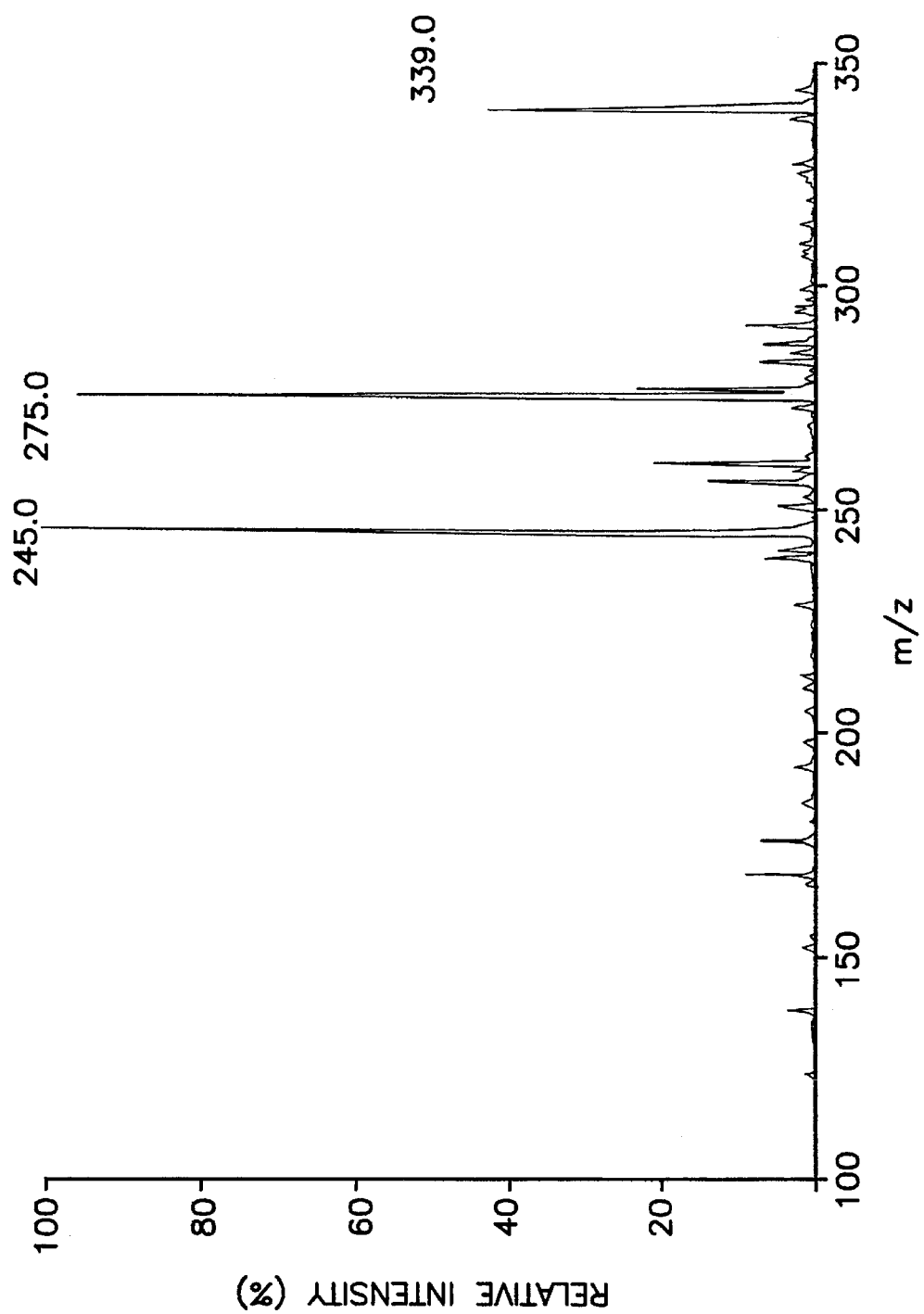
FIGS. 5A, 5B, 5C, and 5D depict the ESI-MS/MS analysis of the mycobacterial antigen for human γδ T cells and stimulation of γδ T cell clone 12G12 by prenyl pyrophosphates.
Figure 5B:
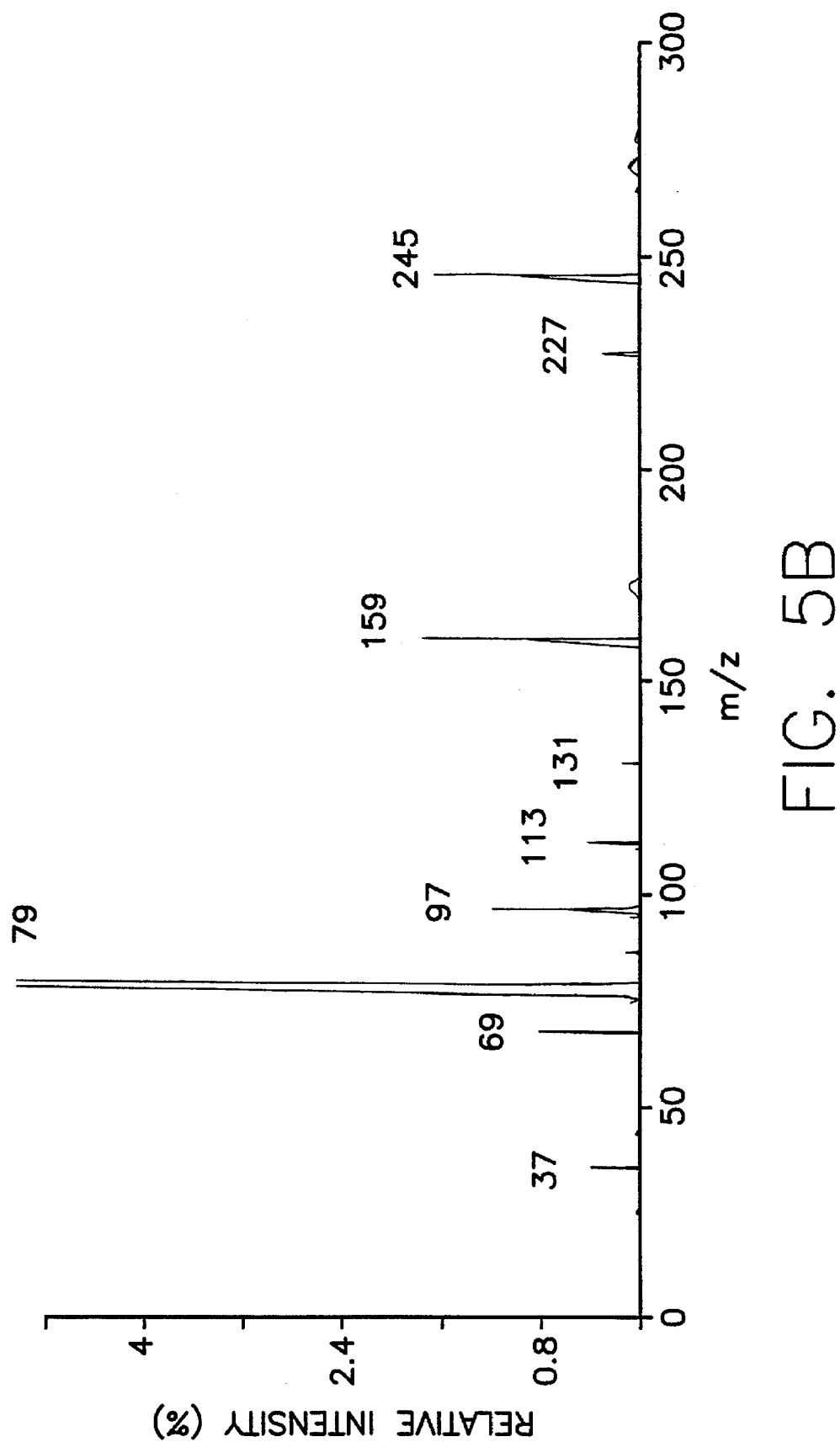
Figure 5C:
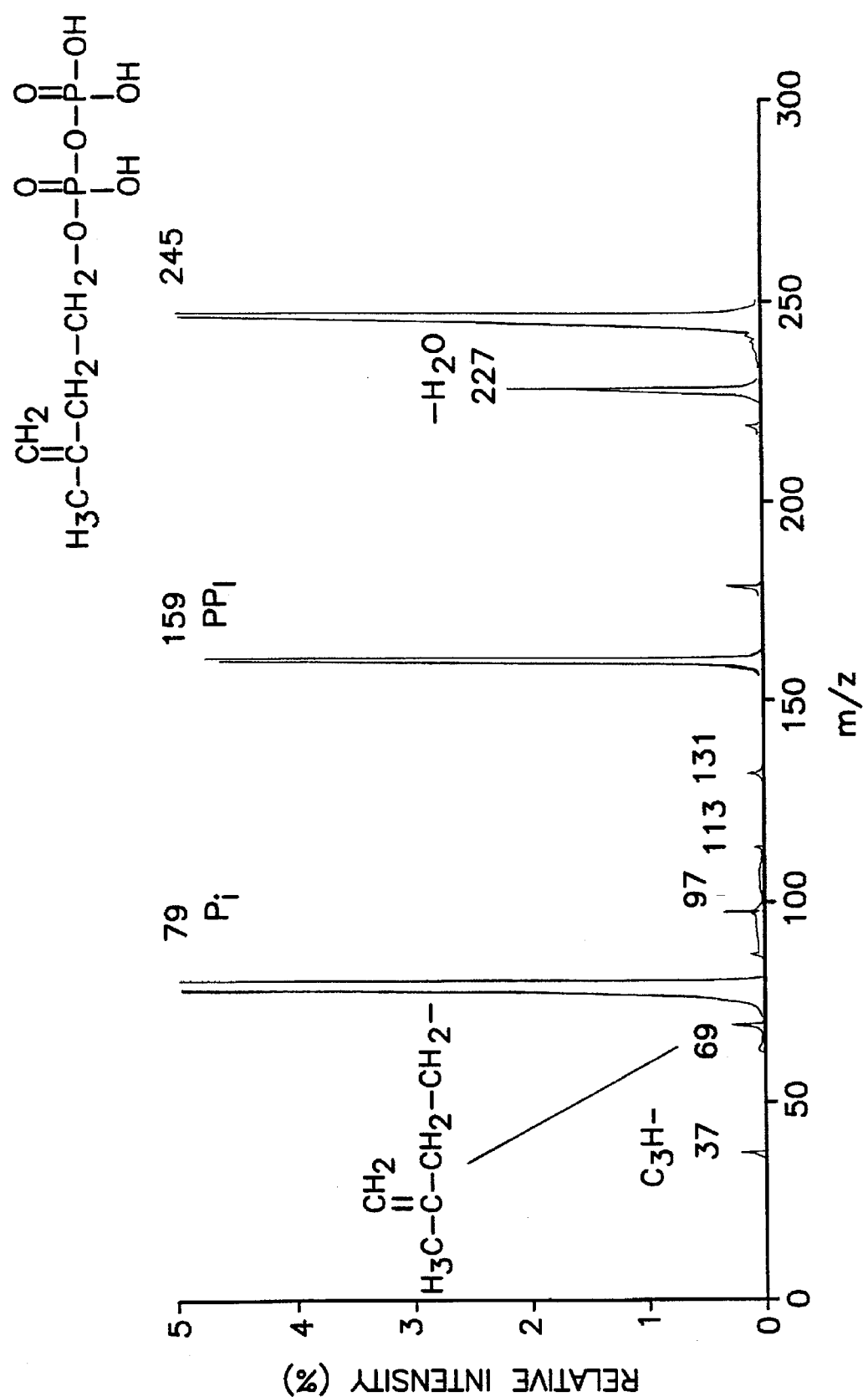
Figure 5D:
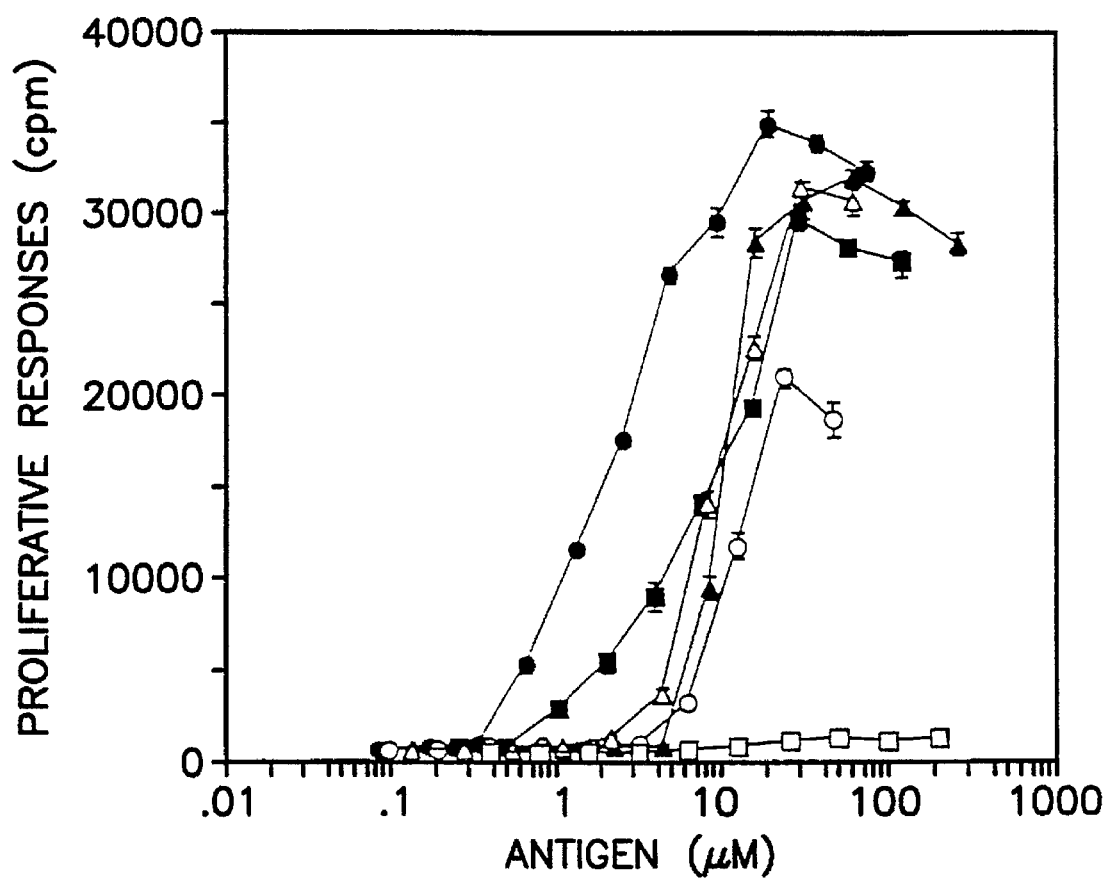
Figure 6A:
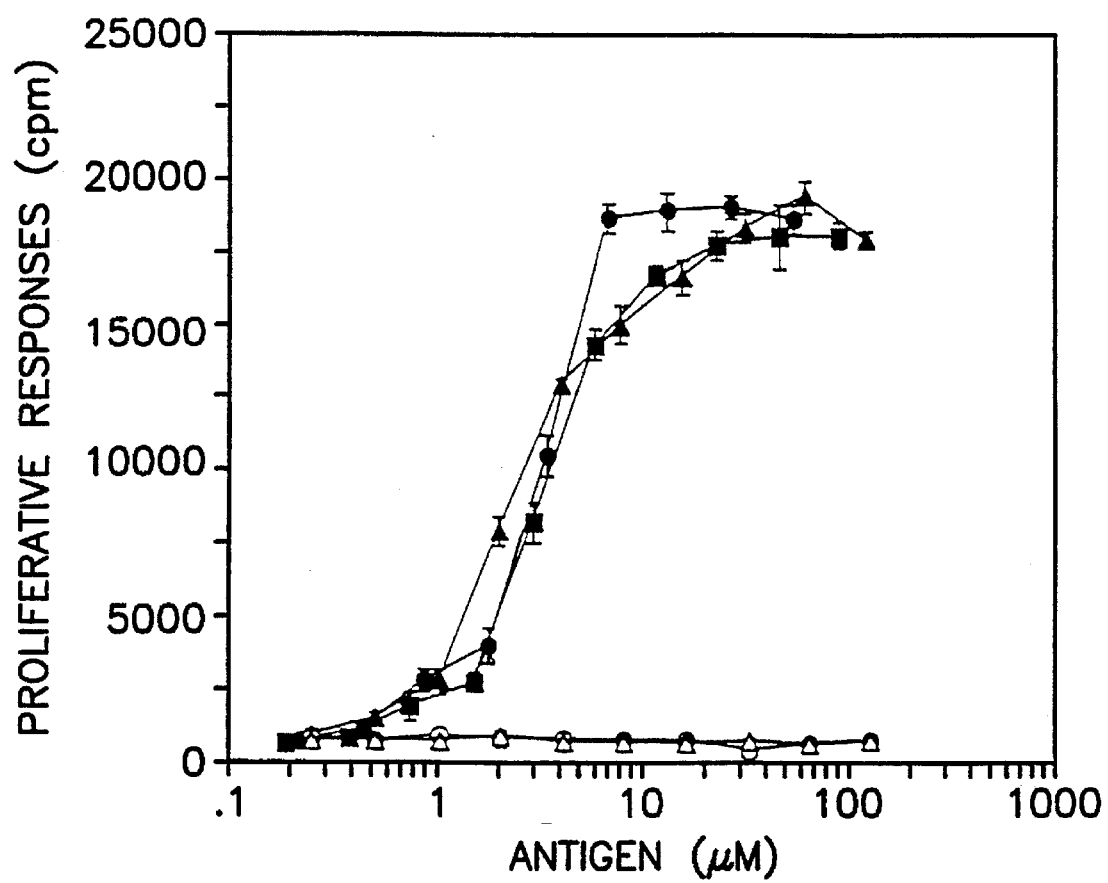
FIGS. 6A, 6B, and 6C depict the recognition of NTP or dNTP γ-derivatives by human γδ T cell clone 12G12 and a schematic diagram of isoprenoid pathways in bacterial and mammalian cells.
Figure 6B:
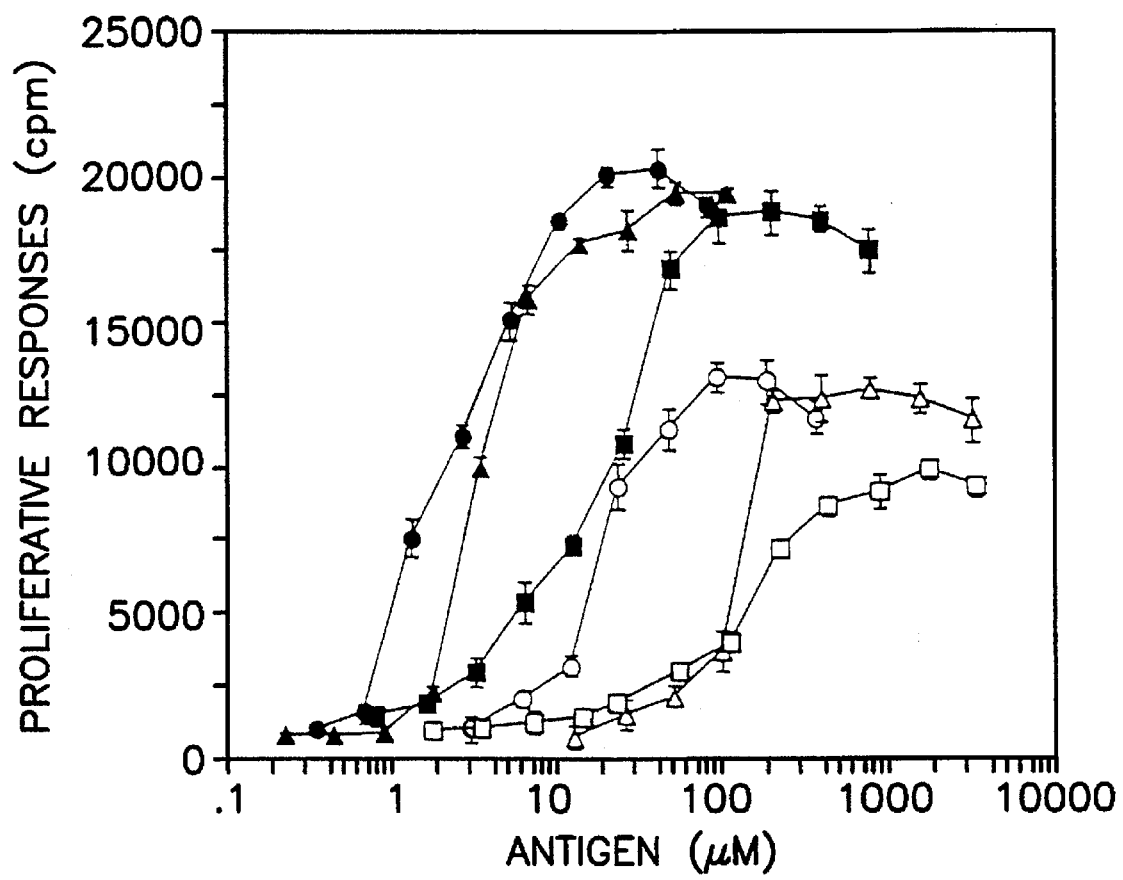
Figure 6C:
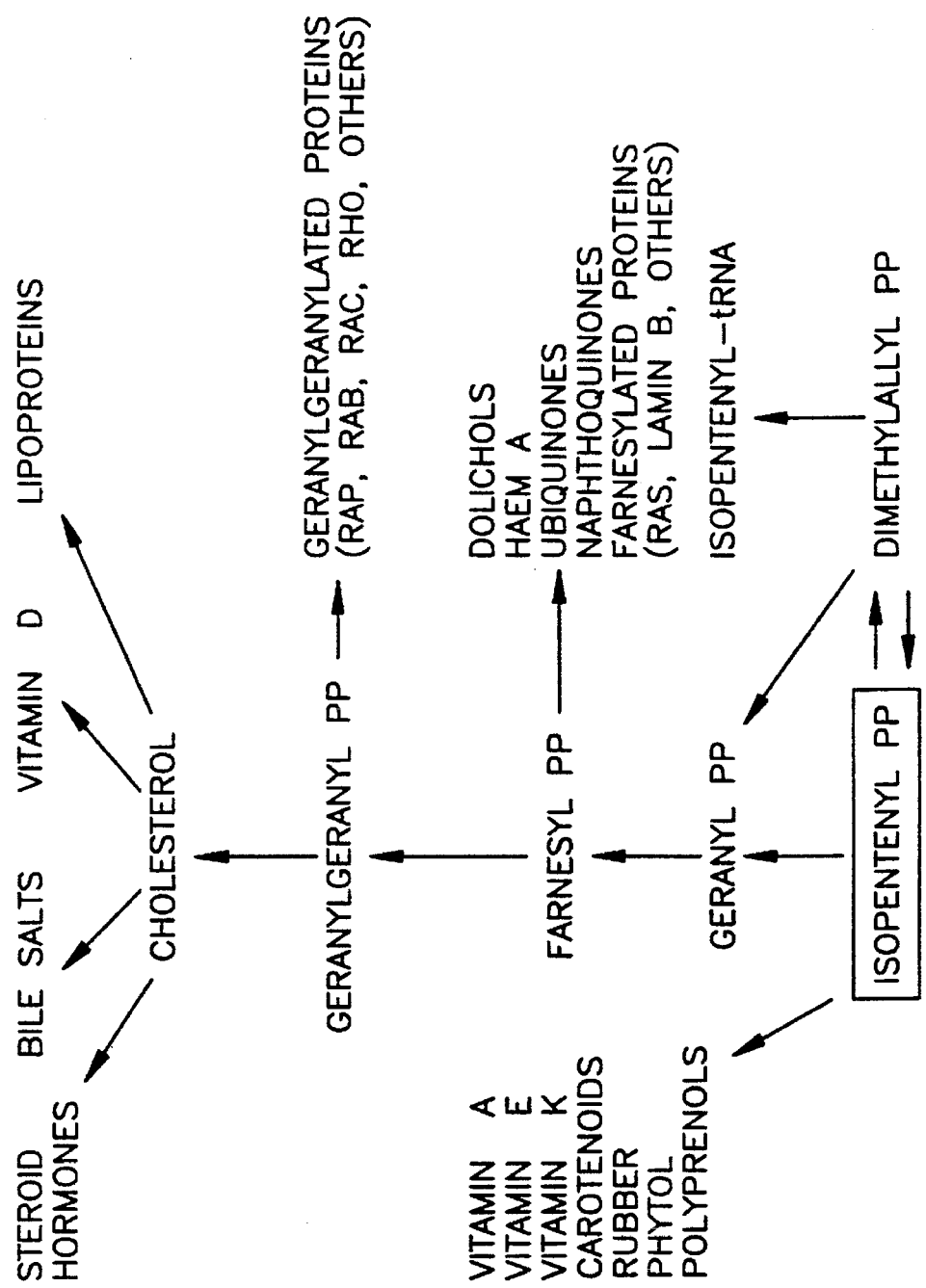

Of the three peaks shown in FIG. 5A, the 339 ion was identified as a hexose diphosphate (immunologically inactive), and the 245 and 275 ions were identified as isopentenyl pyrophosphate and its hydroxymethyl derivative, possibly derived from 5-diphosphomevalonic acid, respectively, based on the daughter ion analysis (data not shown) and synthetic data. The 275 ion was the major pyrophosphorylated ion detected in a highly purified non-peptide antigen preparation from *M. fortutum* (data not shown), suggesting that this compound is also biologically active. To confirm that isopentenyl pyrophosphate is the bioactive molecule, the compound was synthesized as described below, and tested for its ability to stimulate Vγ2Vδ2-bearing T cells. The results establish that the isopentenyl pyrophosphate and related prenyl pyrophosphates exist in mycobacteria as natural ligands for human Vγ2Vδ2-bearing T cells.

III. Synthesis of Phosphate, Pyrophosphate, NTP, and dNTP Derivatives

Alkyl- and Alkenyl- Alcohols. The following alkyl- and alkenyl- alcohols were obtained from Aldrich Chemical Company: ethanol, methanol, 1-propyl alcohol, 1-butyl alcohol, allyl alcohol, crotyl alcohol, dimethylallyl alcohol, isopentenyl alcohol, geraniol, farnesol, and geranylgeranyl alcohol. The 3 methyl-2-pentenyl and 3-methyl-2-hexenyl alcohols were synthesized as described in Ogura, K., et al. *J. Am. Chem. Soc.* 92:20–25 (1970).

Alkyl and Alkenyl Derivatives of Phosphate and Pyrophosphate. Dimethylallyl pyrophosphate, isopentenyl pyrophosphate, geranyl pyrophosphate, farnesyl pyrophosphate, and geranylgeranyl pyrophosphate were obtained from Aldrich Chemical Company. The alkyl and alkenyl derivatives of phosphate and pyrophosphate may also be prepared by allowing ditriethylammonium pyrophosphate to react with the indicated alcohol in the presence of trichloro-acetonitrile as described in Popjak, G., et al. *J. Biol. Chem.* 237:56–61 (1962), and purified by Q SEPHAROSE HP column chromatography (2.5×8 cm) with 0–500 mM triethylammonium bicarbonate buffer, pH 7.5.

NTP and dNTP. Uridine triphosphate (UTP), xanthosine triphosphate (XTP), inosine triphosphate (ITP), guanosine triphosphate (GTP), cytosine triphosphate (CTP), adenosine triphosphate (ATP), 2'-deoxythymidine triphosphate (2'-dTTP), 2',3'-dideoxythymidine triphosphate (2',3'-ddTTP), and 2'-deoxyuridine triphosphate (2'-dUTP) were obtained from Aldrich Chemical Company.

NTP and dNTP γ-Derivatives. NTP and dNTP γ-Derivatives were prepared by allowing the triethylammonium salt of the indicated NTP or dNTP to react with the corresponding alcohol as described in Eckstein, F., et al. *Biochemistry* 23:5225–5232 (1975) and Knorre, D. G., et al. *FEBS Letters* 70:105–108 (1976), and purified by anion exchange chromatography on a Q SEPHAROSE HP column (2.5×8 cm) with 0–500mM triethylammonium bicarbonate buffer, pH 7.5.

IV. Testing of Compounds

The compounds synthesized as described above were tested for their ability to stimulate Vγ2Vδ2-bearing T cells. The results are presented in FIGS. 5D, 6A, 6B, 6C, and Tables 3 and 4 below.

TABLE 3

The Minimal Ligand Concentration (μM) Required for Half-Maximal Proliferative Response of γδ T cell Clone 12G12

| Anchor Chain | Structure | P* | PP* | UTP |
|---|---|---|---|---|
| Methyl- | $CH_3$— | 1800 | 8 | 15 |
| Ethyl- | $CH_3CH_2$— | 240 | 5 | 3 |
| 1-Propyl- | $CH_3CH_2CH_2$— | 1200 | 12 | 12 |
| 2-Propyl- | $(CH_3)_2CH$— | 1600 | 90 | — |
| 1-Butyl- | $CH_3CH_2CH_2CH_2$— | 2000 | 100 | — |
| Allyl- | $CH_2$=$CHCH_2$— | 800 | 5 | 4 |
| Crotyl- | $CH_3CH$=$CHCH_2$— | 350 | 8 | 3 |
| Dimethyl-allyl- | $(CH_3)_2C$=$CHCH_2$— | 30 | 10 | 0.3 |
| Iso-pentenyl- | $CH_2$=$C(CH_3)CH_2CH_2$— | 700 | 3 | 4 |
| Geranyl- | $H(CH_2C(CH)_3$=$CHCH_2)_2$— | 800 | 10 | 8 |
| Farnesyl- | $H(CH_2C(CH)_3$=$CHCH_2)_3$— | — | 10 | — |
| Geranyl-geranyl- | $H(CH_2C(CH)_3$=$CHCH_2)_4$— | — | 10 | — |
| 3-Methyl-2-pentenyl- | $CH_3CH_2C(CH_3)$=$CHCH_2$— | — | 8 | — |
| 3-Methyl-2-hexenyl- | $CH_3CH_2CH_2C(CH_3)$=$CHCH_2$— | — | 0.3 | — |

*P is phosphate and PP is pyrophosphate.

TABLE 4

The Minimal Ligand Concentration (μM) Required for Half-Maximal Proliferative Response of γδ T cell Clone 12G12

| Ethyl Derivatives of dNTP and NTP | Concentration (μM) |
|---|---|
| 2'-dTTP | 3 |
| 2',3'-ddTTP | 4 |
| 2'-dUTP | 3 |
| UTP | 3 |
| XTP | 4 |
| ITP | 20 |
| GTP | 20 |
| CTP | 120 |
| ATP | 200 |

All publications mentioned hereinabove are hereby incorporated in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for stimulating the proliferation of Vγ2Vδ2 T cells in a mammal comprising administering to the mammal a Vγ2Vδ2 T cell proliferation stimulating amount of a monoalkyl- or alkenyl- pyrophosphate having the formula ROPO(OH)OPO(OH)$_2$ wherein R is a C1–C4 straight or branched chain alkyl, or a C2–C20 straight or branched chain alkenyl.

2. The method of claim 1, wherein the monoalkyl pyrophosphate is selected from the group consisting of methyl pyrophosphate, ethyl pyrophosphate, n-propyl pyrophosphate, n-butyl pyrophosphate and isopropyl pyrophosphate.

3. The method of claim 2, wherein the monoalkyl pyrophosphate is ethyl pyrophosphate.

4. The method of claim 1, wherein the alkenyl pyrophosphate is selected from the group consisting of allyl pyrophosphate, crotyl pyrophosphate, dimethylallyl pyrophosphate, isopentenyl pyrophosphate, geranyl pyrophosphate, farnesyl pyrophosphate, geranylgeranyl pyrophosphate, 3-methyl-2-pentenyl pyrophosphate, and 3-methyl-2-hexenyl pyrophosphate.

5. The method of claim 4, wherein the alkenyl pyrophosphate is 3-methyl-2-hexenyl pyrophosphate.

6. The method of claim 1, wherein the mammal has a disease expressing antigens recognized by Vγ2Vδ2 T cells.

7. The method of claim 6, wherein the disease is selected from the group consisting of leukemia, lymphoma, tuberculosis, leprosy, malaria, AIDS, rheumatoid arthritis, ulcerative colitis and anemia.

8. The method of claim 6, wherein the route of administration is oral, intravenous, intramuscular, subcutaneous or intraperitoneal administration.

9. A method for stimulating the proliferation of Vγ2Vδ2 T cells in a mammal comprising administering to the mammal biological fluid from the mammal that has been treated with a Vγ2Vδ2 T cell proliferation stimulating amount of a monoalkyl- or alkenyl-pyrophosphate having the formula ROPO(OH)OPO(OH)$_2$ wherein R is a C1–C4 straight or branched chain alkyl, or a C2–C20 straight or branched chain alkenyl.

10. The method of claim 9, wherein the monoalkyl pyrophosphate is selected from the group consisting of methyl pyrophosphate, ethyl pyrophosphate, n-propyl pyrophosphate, n-butyl pyrophosphate and isopropyl pyrophosphate.

11. The method of claim 10, wherein the monoalkyl pyrophosphate is ethyl pyrophosphate.

12. The method of claim 9, wherein the alkenyl pyrophosphate is selected from the group consisting of allyl pyrophosphate, crotyl pyrophosphate, dimethylallyl pyrophosphate, isopentenyl pyrophosphate, geranyl pyrophosphate, farnesyl pyrophosphate, geranylgeranyl pyrophosphate, 3-methyl-2-pentenyl pyrophosphate, and 3-methyl-2-hexenyl pyrophosphate.

13. The method of claim 12, wherein the alkenyl pyrophosphate is 3-methyl-2-hexenyl pyrophosphate.

14. The method of claim 9, wherein the mammal has a disease expressing antigens recognized by Vγ2Vδ2 T cells.

15. The method of claim 14, wherein the disease is selected from the group consisting of leukemia, lymphoma, tuberculosis, leprosy, malaria, AIDS, rheumatoid arthritis, ulcerative colitis and anemia.

* * * * *